US00PP13652P2

(12) United States Plant Patent
DePew et al.

(10) Patent No.: US PP13,652 P2
(45) Date of Patent: Mar. 11, 2003

(54) SEASHORE DROPSEED PLANT NAMED 'BT-1'

(75) Inventors: Michael DePew, Tekonsha, MI (US); Stewart Bennett, Bokeelia, FL (US); Paul H. Tillman, Bokeelia, FL (US)

(73) Assignee: Enviro-Turf, L C, Tekonsha, MI (US)

( * ) Notice: Subject to any disclaimer, the term of this patent is extended or adjusted under 35 U.S.C. 154(b) by 0 days.

(21) Appl. No.: 09/643,598

(22) Filed: Aug. 22, 2000

(51) Int. Cl.[7] ..... A01H 5/00

(52) U.S. Cl. ..... Plt./384

(58) Field of Search ..... Plt./384

(56) References Cited

PUBLICATIONS

U.S. patent application Ser. No. 09/759,481, DePew et al., filed Jan. 12, 2001.
U.S. patent application Ser. No. 09/643,286, DePew et al., filed Aug. 22, 2000.
U.S. patent application Ser. No. 09/502,904, Bennett et al., filed Feb. 11, 2000.
U.S. patent application Ser. No. 09/502,903, Bennett et al., filed Feb. 11, 2000.

*Primary Examiner*—Bruce R. Campell
*Assistant Examiner*—Annette H. Para
(74) *Attorney, Agent, or Firm*—Laura G. Barrow

(57) ABSTRACT

A novel seashore dropseed (*Sporobolus virginicus*) cultivar ('BT-l') is disclosed. The 'BT-1' cultivar is characterized by enhanced turf quality under mown and high traffic stress conditions; improved, darker green leaf color; lower growth habit; denser, more tightly knit sod; low mow height tolerance; finer-textured leaf blades; and increased saline and drought tolerance.

7 Drawing Sheets

SUMMARY OF THE INVENTION

The present invention relates to a new cultivar of seashore dropseed (*Sporobolus virginicus*) that is particularly suited as a turf grass for recreational fields and golf courses. The new cultivar of the present invention is herein referred to by its cultivar name 'BT-1'.

The 'BT-1' cultivar is a low growing halophytic grass spreading by rhizomes and stolons. The grass is particularly well suited for use on golf courses in all areas, including tees mowed to ½ inch, fairways and roughs mowed to ½ to 2 inches, and for putting greens mowed to 3/16 inch. It also suitable for grass tennis courts, lawn bowling lawns and athletic fields, or any other area where a fine textured, low growing turf with superior salt tolerance is desired.

BRIEF DESCRIPTION OF THE DRAWINGS

FIG. 1 is a photograph of a single seed head of the 'BT-1' variety.

FIG. 2 is a photograph 'BT-1' variety showing rhizomanos growth habit.

FIG. 3 is a photograph of seed heads of Florida native seashore dropseed.

FIG. 4 is a photograph of the 'BT-1' variety in an unmown state.

FIG. 5 is a photograph of a field section of the 'BT-1' variety maintained at ½ inch mown height.

DETAILED DESCRIPTION OF THE VARIETY

Figure 6:
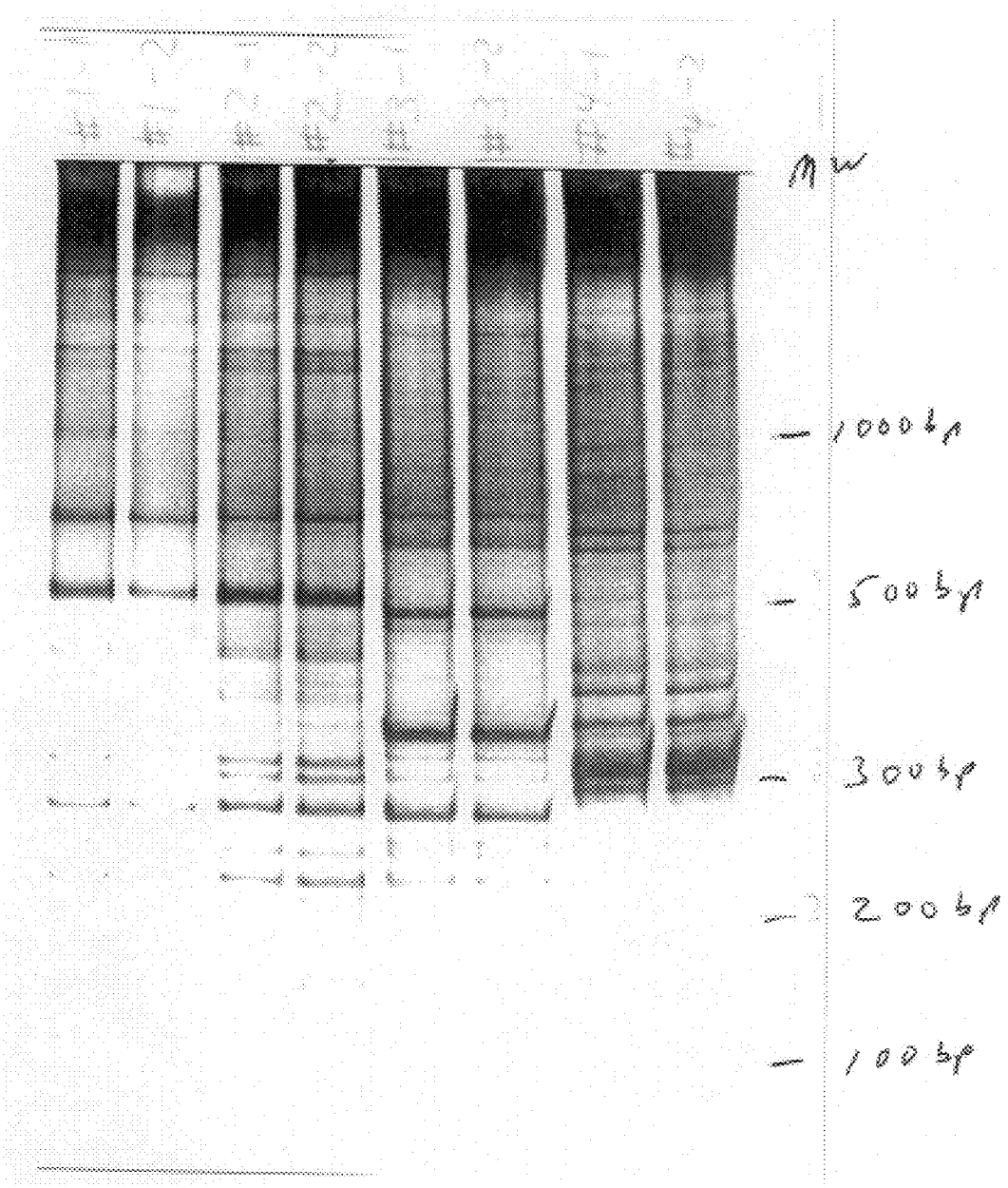
FIG. 6 shows DNA amplification profiles of 'BT-1' and a Florida native seashore dropseed using an 10.6e primer.

The following is a detailed description of the new grass variety based upon observation of the grass grown in field plots and under live golf conditions on a local golf course.

Asexual Reproduction

The process of developing the cultivars of the present invention began with the selection of a grass discovered from a closed sand mine site in Barbuda of the West Indies. The mine site was a man-disturbed area of land that comprised flat stretches of sandy soil after mining (prior to mining, the area comprised rolling sand dunes). An initial selection of a seashore dropseed ecotype was made on a grassy area of the mine site located between a parking lot and building, the grassy area having been maintained periodically by mowing. This initial selection of grass was based upon its fine texture, dark green color, drought resistance, and overall turf characteristics compared to common native ecotypes. This initial ecotype discovered by the inventors was not typical of other native ecotypes found growing on non-disturbed, uncultivated sites within the same vicinity but not on the mine site, the other native ecotypes being much coarser in texture.

The initial selection found on the mine site was asexually propagated and evaluated in Barbuda, West Indies for golf and lawn applications. Specifically, this initial ecotype selection was transplanted into mixed colonies of other seashore dropseed ecotypes found on other parts of the mine site. The respective ecotypes were allowed to cross and produce seeds. The seeds were collected and planted, with the resulting grasses evaluated in observation plots. These observation plots were maintained under salt water irrigated conditions with cultural conditions comparable to an athletic field or golf course fairway. Promising entries were evaluated by their saline tolerance, fresh water tolerance, and turf quality ratings (previous genotypes performed poorly as a high quality mowed turf grass under traffic stress and varying salinity regimes, many such genotypes being obligate halophytes), as discussed further below.

Plants of top entries were sprigged into observation plots representing multiple use conditions (i.e. golf course tees and greens; residential lawns), different management protocols (i.e. high fertility vs. low fertility; high traffic stress vs. low traffic stress; varying salinity; etc.). Top plant entries developed in Barbuda were collected as seed from isolated plots and transferred to Florida for further evaluation. The seeds were planted in Florida, and from the germinated turf plants, specific individuals cultivars were selected and asexually propagated into test plots and seed stock propagation beds. Here, the top entries were placed in mixed colony (i.e. two genotypes) observation plots with progeny asexually reproduced and collected from within these plots, isolated, and re-established into additional observation plots.

Improved entries and selections from the Florida plots described in the preceding paragraph were evaluated and compared to Florida native seashore dropseed. Three initial improved cultivars were developed from this program, including BT-1. Improved characteristics include (1) darker green leaf color; (2) finer-textured, narrower leaf blades; (3) lower growth habit; (4) denser more tightly knit sod; (5) enhanced turf quality; (6) low mow height tolerance; and (7) enhanced traffic/wear tolerance. The age of the plant observed for botanical description was approximately 180 days old. All subsequent asexual reproductions of the BT-1 cultivar observed to date have been true to the original variety. The BT- 1variety has been asexually propagated by the applicants as sprigs, plugs, and sod.

Botanical Description

The BT-1 cultivar is a perennial grass. The grass stems normally have only one or two nodes under mown conditions. The grass stems have overlapping sheath margins and arise singly or in small clusters from widely spreading yellowish rhizomes. The sheaths have a few long hairs on either side of the collar. Leaves are arranged in a distinctly distichous arrangement. Leaf veins are prominent, and leaf margins are smooth. The grass blades have a dark green color, Munsell color designation 5GY 5/4 adaxial, 5GY 4/6 abaxial. The grass blades are typically 1.5 to 3.5 cm long (umnown) and 0.8 to 2.0 mm wide. The ligule is a minute fringed membrane. Sheaths are pilose near the throat. Auricles are absent, and the collar is smooth. Upon flowering, the culms are about 4 to 6 cm tall with inflorescence forming a contracted, spike-like, densely flowered panicle with racemes having a length of 1 to 2.5 cm. Spikelets are flowered, awnless, straw colored or grayish, or purple tinged, hairless, and shiny. Seeds are a pale straw color and about 1.5 to 2 mm in length.

General Observations

The 'BT-1' cultivar has shown to be particularly well suited for use on golf tees and fairways. This grass has been tested under long term saline irrigation up to 35,000 ppm and has also survived seawater flooding from tropical storms and hurricanes. The applicants have also utilized periodic seawater and brine water (45,000 ppm) drenches on putting green surfaces for pest and weed control with no apparent damage to the grass. Direct applications of table salt or sea salt have also been employed for weed control, although temporary burning of the grass leaf tips have been observed with heavy salt applications.

Compared to hybrid bermudagrasses (notably 'Tifway' and 'Tifgreen') which are utilized for similar purposes, the 'BT-1' cultivar has foremost greater salinity tolerance and, under saline conditions, improved density, finer texture, greater sod strength, increased rooting, and improved color. This grass has enhanced qualities for drought tolerance, surviving for more than six months without the addition of soil moisture. The grass also has adaptations for moderate to heavy shade tolerance.

Compared to native *Sporobolus virginicus*, the 'BT-1' variety has a finer, darker green texture and enhanced tolerance to low mow heights. Native *Sporobolus virginicus* and the 'BT-1' variety do share similar traits for salinity, shade, and drought tolerance.

DNA Analysis

Figure 7:
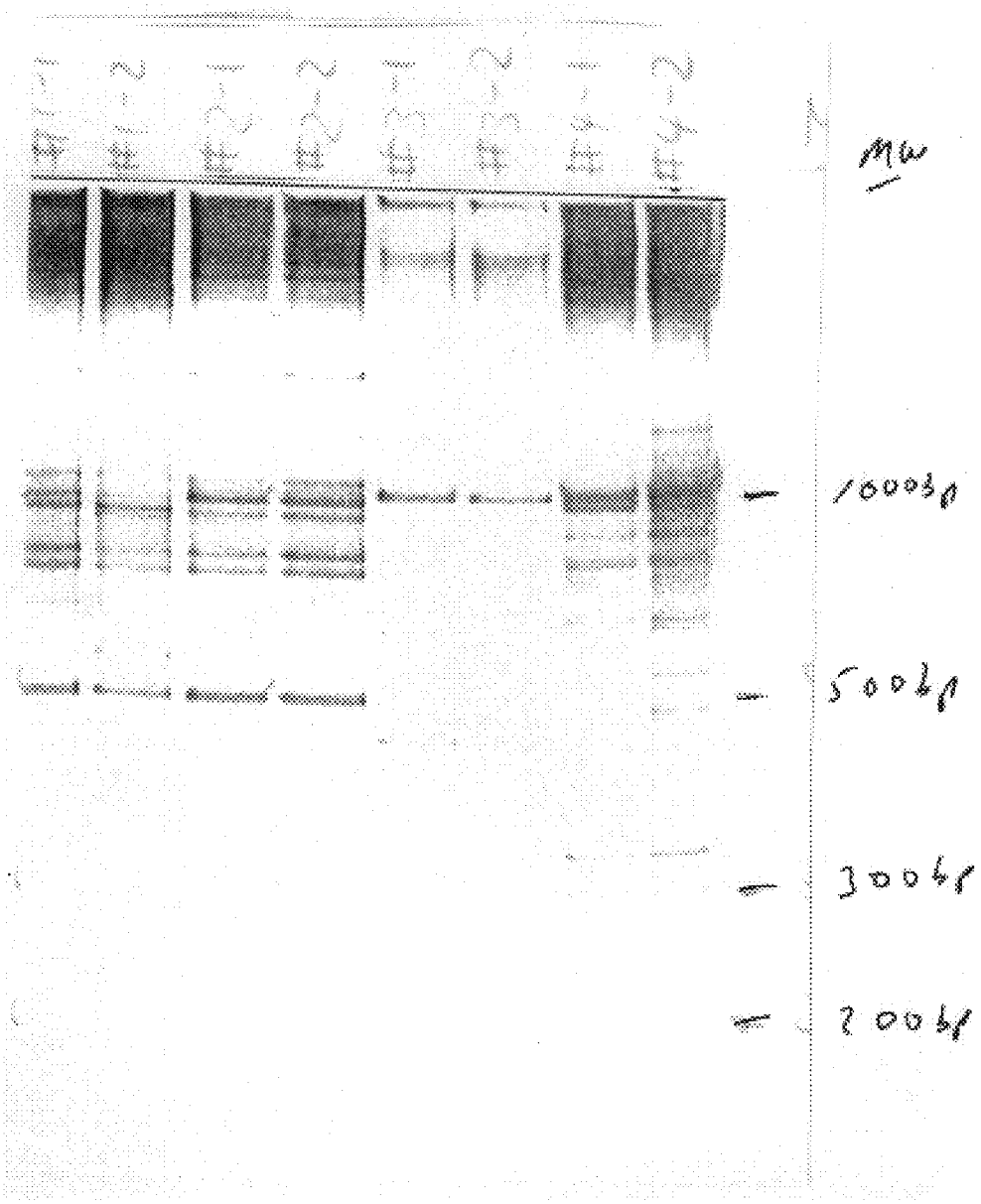
FIG. 7 shows DNA amplification profiles of 'BT-1 ' and a Florida native seashore dropseed using an 8.6i primer.

Comparative DNA amplification profiles of the 'BT-1' cultivar, Florida native seashore dropseed, and two seashore paspalum cultivars (#1-1, #1-2, #2-1, and #2-2) produced by the University of Tennessee Plant Molecular Genetics laboratory are shown in FIGS. 6–7. "#3-1" and "#3-2" are profiles for the 'BT-1' grass and "#4-1" and "#4-2" are profiles for native Florida seashore dropseed. The profiles were generated using known DAF techniques with two different primers (10.6e —FIG. 6 and 8.6i- FIG. 7) (see e.g., Caetano-Anolles, et al. *Bio/Technology* 9:553–557 (1991); U.S. Pat. No. 5,413,909; Bassam and Bentley, *Biotechniques* 19:568–573; U.S. Pat. No. 5,643,479). Based upon these results, it has been determined that the applicants' 'BT-1' grass is genetically different from the native Florida grass.

We claim:

1. A new and distinct cultivar of seashore dropseed plant, substantially as herein illustrated and described, characterized by its enhanced turf quality under mown and high traffic stress conditions; improved, darker green leaf color; lower growth habit; denser, more tightly knit sod; low mow height tolerance; finer-textured leaf blades; and superior tolerance to saline, drought, and shade conditions.

* * * * *